United States Patent
Bodner

(10) Patent No.: US 8,046,084 B2
(45) Date of Patent: *Oct. 25, 2011

(54) EXTENDABLE/RETRACTABLE LEAD HAVING DOWNSIZED LEAD BODY

(75) Inventor: Jeffrey P. Bodner, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1130 days.

This patent is subject to a terminal disclaimer.

(21) Appl. No.: 11/780,398

(22) Filed: Jul. 19, 2007

(65) Prior Publication Data

US 2008/0011504 A1   Jan. 17, 2008

Related U.S. Application Data

(63) Continuation of application No. 09/870,376, filed on May 30, 2001, now Pat. No. 7,257,449.

(51) Int. Cl.
*A61N 1/08* (2006.01)
(52) U.S. Cl. ........................................................ 607/119
(58) Field of Classification Search .................. 600/373, 600/374, 377; 607/115, 116, 119, 122
See application file for complete search history.

(56) References Cited

U.S. PATENT DOCUMENTS

| | | | |
|---|---|---|---|
| 4,295,270 A | 10/1981 | Cammarata | |
| 4,452,254 A | 6/1984 | Goldberg et al. | |
| 4,547,193 A | 10/1985 | Rydell | |
| 4,559,951 A | 12/1985 | Dahl et al. | |
| 4,640,983 A | 2/1987 | Comte | |
| 4,699,157 A | 10/1987 | Shonk | |
| 4,840,186 A | 6/1989 | Lekholm et al. | |
| 4,960,134 A | 10/1990 | Webster, Jr. | |
| 5,005,587 A | 4/1991 | Scott | |
| 5,014,721 A | 5/1991 | Hirschberg | |
| 5,040,544 A * | 8/1991 | Lessar et al. ............... | 607/122 |
| 5,057,092 A | 10/1991 | Webster | |
| 5,181,920 A | 1/1993 | Mueller et al. | |
| 5,275,171 A | 1/1994 | Barcel | |
| 5,336,254 A | 8/1994 | Brennen et al. | |
| 5,397,304 A | 3/1995 | Truckai | |
| 5,425,755 A | 6/1995 | Doan | |
| 5,476,498 A | 12/1995 | Ayers | |
| 5,487,757 A | 1/1996 | Truckai et al. | |

(Continued)

FOREIGN PATENT DOCUMENTS

EP   0709111   5/1996

OTHER PUBLICATIONS

Supplemental Notice of Allowability mailed Jul. 3, 2007 in U.S. Appl. No. 10/717,978, 4 pages.

(Continued)

*Primary Examiner* — Carl H Layno
*Assistant Examiner* — Frances Oropeza
(74) *Attorney, Agent, or Firm* — Faegre & Benson LLP

(57) ABSTRACT

A lead assembly includes a flexible lead body extending from a proximal end to a distal end, and the lead body includes two or more conductors disposed therein. The second conductor is disposed within the first conductor, and the first conductor has a coating of insulation disposed on a portion thereof. In another option, a sleeve of insulative material is disposed between the first conductor and the second conductor.

17 Claims, 4 Drawing Sheets

U.S. PATENT DOCUMENTS

| | | | |
|---|---|---|---|
| 5,545,200 | A | 8/1996 | West et al. |
| 5,545,201 | A * | 8/1996 | Helland et al. ............... 607/127 |
| 5,554,178 | A | 9/1996 | Dahl et al. |
| 5,569,220 | A | 10/1996 | Webster |
| 5,591,142 | A | 1/1997 | Van Erp |
| 5,609,621 | A | 3/1997 | Bonner |
| 5,628,774 | A | 5/1997 | Helland et al. |
| 5,662,621 | A | 9/1997 | Lafontaine |
| 5,674,272 | A | 10/1997 | Bush et al. |
| 5,680,860 | A | 10/1997 | Imran |
| 5,755,762 | A | 5/1998 | Bush |
| 5,779,699 | A | 7/1998 | Lipson |
| 5,796,044 | A * | 8/1998 | Cobian et al. ............... 174/103 |
| 5,814,090 | A | 9/1998 | Latterell et al. |
| 5,843,076 | A | 12/1998 | Webster, Jr. et al. |
| 5,843,149 | A | 12/1998 | Ebert et al. |
| 5,845,396 | A | 12/1998 | Altman et al. |
| 5,851,226 | A | 12/1998 | Skubitz et al. |
| 5,865,791 | A | 2/1999 | Whayne et al. |
| 5,882,346 | A | 3/1999 | Pomeranz et al. |
| 5,891,135 | A | 4/1999 | Jackson et al. |
| 5,891,136 | A | 4/1999 | McGee et al. |
| 5,921,982 | A | 7/1999 | Lesh et al. |
| 5,925,038 | A | 7/1999 | Panescu et al. |
| 5,931,862 | A | 8/1999 | Carson |
| 5,984,917 | A | 11/1999 | Fleischman et al. |
| 6,002,969 | A | 12/1999 | Machek et al. |
| 6,051,017 | A | 4/2000 | Loeb et al. |
| 6,052,625 | A | 4/2000 | Marshall |
| 6,055,457 | A | 4/2000 | Bonner |
| 6,083,216 | A | 7/2000 | Fischer, Sr. |
| 6,104,961 | A | 8/2000 | Conger et al. |
| 6,122,552 | A | 9/2000 | Tockman et al. |
| 6,132,438 | A | 10/2000 | Fleischman et al. |
| 6,181,965 | B1 | 1/2001 | Loeb et al. |
| 6,213,995 | B1 | 4/2001 | Steen et al. |
| 6,217,528 | B1 | 4/2001 | Koblish et al. |
| 6,249,708 | B1 | 6/2001 | Nelson et al. |
| 6,249,709 | B1 | 6/2001 | Conger et al. |
| 6,256,542 | B1 | 7/2001 | Marshall et al. |
| 6,259,954 | B1 | 7/2001 | Conger et al. |
| 6,295,476 | B1 | 9/2001 | Schaenzer |
| 6,326,587 | B1 | 12/2001 | Cardineau et al. |
| 6,445,958 | B1 | 9/2002 | Machek et al. |
| 6,477,428 | B1 | 11/2002 | Skinner et al. |
| 6,606,522 | B2 | 8/2003 | Schell |
| 6,701,191 | B2 | 3/2004 | Schell |
| 7,257,449 | B2 * | 8/2007 | Bodner .................... 607/122 |
| 2001/0044646 | A1 | 11/2001 | Marshall et al. |
| 2002/0183822 | A1 | 12/2002 | Bodner |
| 2004/0230277 | A1 | 11/2004 | Schell |

OTHER PUBLICATIONS

"Application U.S. Appl. No. 09/870,369, Amendment and Response filed Oct. 8, 2002 to Non-Final Office Action mailed Jul. 8, 2002", 8 pgs.

"Application U.S. Appl. No. 09/870,369, Amendment and Response filed Apr. 14, 2003 to Non-Final Office Action mailed Jan. 14, 2003", 13 pgs.

"Application U.S. Appl. No. 09/870,369, Interview Summary mailed Feb. 27, 2003", 2 pgs.

"Application U.S. Appl. No. 09/870,369, Non-Final Office Action mailed Jan. 14, 2003", 11 pgs.

"Application U.S. Appl. No. 09/870,369, Non-Final Office Action mailed Jul. 8, 2002", 6 pgs.

"Application U.S. Appl. No. 09/870,369, Notice of Allowance mailed Aug. 11, 2003", 10 pgs.

"Application U.S. Appl. No. 09/870,369, Notice of Incomplete Response mailed Jul. 15, 2003", 3 pgs.

"Application U.S. Appl. No. 09/870,369, Response to Office Action filed Sep. 4, 2003", 1 pg.

"Application U.S. Appl. No. 09/870,376, Response filed Jul. 21, 2003 to Final Office Action mailed May 21, 2003", 10 pgs.

"Application U.S. Appl. No. 09/870,376, Advisory Action mailed Jul. 21, 2006", 3 pgs.

"Application U.S. Appl. No. 09/870,376, Advisory Action mailed Aug. 7, 2003", 3 pgs.

"Application U.S. Appl. No. 09/870,376, Amendment and Response filed Dec. 10, 2004 to Non-Final Office Action mailed Sep. 10, 2004", 12 pgs.

"U.S. Appl. No. 09/870,376, Amendment and Response filed Mar. 15, 2006 to Non-Final Office Action mailed Dec. 15, 2005", 17 pgs.

"U.S. Appl. No. 09/870,376, Amendment and Response filed Mar. 31, 2003 to Non-Final Office Action mailed Dec. 31, 2002", 10 pgs.

"U.S. Appl. No. 09/870,376, Amendment and Response filed Jul. 10, 2006 to Final Office Action mailed Apr. 18, 2006", 17 pgs.

"U.S. Appl. No. 09/870,376, Amendment and Response filed Sep. 22, 2005 to Non-Final Office Action mailed Jun. 22, 2005", 24 pgs.

"U.S. Appl. No. 09/870,376, Final Office Action mailed Feb. 15, 2005", 14 pgs.

"U.S. Appl. No. 09/870,376, Final Office Action mailed Apr. 18, 2006", 7 pgs.

"U.S. Appl. No. 09/870,376, Final Office Action mailed May 21, 2003", 8 pgs.

"U.S. Appl. No. 09/870,376, Interview Summary mailed Jun. 1, 2005", 4 pgs.

"U.S. Appl. No. 09/870,376, Non-Final Office Action mailed Jan. 5, 2004", 9 pgs.

"U.S. Appl. No. 09/870,376, Non-Final Office Action mailed Oct. 18, 2006", 6 pgs.

"U.S. Appl. No. 09/870,376, Non-Final Office Action mailed Dec. 15, 2005", 9 pgs.

"U.S. Appl. No. 09/870,376, Non-Final Office Action mailed Dec. 31, 2002", 7 pgs.

"U.S. Appl. No. 09/870,376, Non-Final Office Action mailed Jun. 22, 2005", 11 pgs.

"U.S. Appl. No. 09/870,376, Non-Final Office Action mailed Sep. 10, 2004", 9 pgs.

"U.S. Appl. No. 09/870,376, Notice of Allowance mailed Apr. 4, 2007", 6 pgs.

"U.S. Appl. No. 09/870,376, Request for Continued Examination and Amendment filed Nov. 20, 2003", 11 pgs.

"U.S. Appl. No. 09/870,376, Response filed Jan. 18, 2007 to Non-Final Office Action mailed Oct. 18, 2006", 14 pgs.

"U.S. Appl. No. 09/870,376, Response filed Apr. 5, 2004 to Non-Final mailed Jan. 5, 2004", 11 pgs.

"U.S. Appl. No. 09/870,376, Response filed Jun. 6, 2005 to Final mailed Feb. 15, 2005", 13 pgs.

"U.S. Appl. No. 10/717,978, Amendment and Response filed Oct. 20, 2006 to Non-Final mailed Jun. 19, 2006", 15 pgs.

"U.S. Appl. No. 10/717,978, Amendment and Response filed Dec. 22, 2005 to Non-Final Office Action mailed Sep. 22, 2005", 16 pgs.

"U.S. Appl. No. 10/717,978, Amendment and Response filed May 21, 2007 to Non-Final Office Action mailed Jan. 19, 2007", 12 pgs.

"U.S. Appl. No. 10/717,978, Interview Summary filed Jul. 12, 2007", 1 pg.

"U.S. Appl. No. 10/717,978, Non-Final Office Action mailed Jan. 19, 2007", 5 pgs.

"U.S. Appl. No. 10/717,978, Non-Final Office Action mailed Jun. 19, 2006", 5 pgs.

"U.S. Appl. No. 10/717,978, Notice of Allowance mailed Jun. 14, 2007", 6 pgs.

"U.S. Appl. No. 10/717,978, Office Action mailed Sep. 22, 2005", 6 pgs.

"U.S. Appl. No. 10/717,978, Preliminary Amendment mailed Jun. 17, 2004", 6 pgs.

"U.S. Appl. No. 10/717,978, Notice of Allowance mailed Sep. 21, 2007", 4 pgs.

"PCT Application No. PCT/US00/10102, International Search Report mailed Aug. 16, 2000", 5 pgs.

"PCT Application No. PCT/US00/10102, Written Opinion mailed Jan. 12, 2001", 9 pgs.

* cited by examiner

EXTENDABLE/RETRACTABLE LEAD HAVING DOWNSIZED LEAD BODY

CROSS-REFERENCE TO RELATED APPLICATIONS

This application is a continuation of U.S. patent application Ser. No. 09/870,376, filed on May 30, 2001, now issued as U.S. Pat. No. 7,257,449 the specification of which is incorporated herein by reference.

This application is related to U.S. patent application Ser. No. 09/870,369, filed on May 30, 2001, now issued as U.S. Pat. No. 6,701,191, and to U.S. patent application Ser. No. 10/717,978, each of which is incorporated herein by reference.

TECHNICAL FIELD

The present invention relates generally to leads for stimulating or monitoring tissue. More particularly, it pertains to an extendable/retractable lead having a downsized lead body.

BACKGROUND

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle.

Cardiac pacing may be performed by the transvenous method or by leads implanted directly onto the epicardium. Permanent transvenous pacing is performed using a lead positioned within one or more chambers of the heart. One or more leads may be positioned in the ventricle or in the atrium through a subclavian vein, and the lead terminal pins are attached to a pacemaker, which is implanted subcutaneously.

The leads include an outer insulative lead body for electrically insulating the conductor, and allowing only the electrodes to make electrical contact with the body tissue. The insulation of the conductor must be reliable, to prevent inadvertent shorting of the conductor. The outer insulation affects the several aspects of the lead structure, for example, lead flexibility and abrasion resistance, and the outer dimensions of the lead body. It is preferable that the lead is flexible since, the more flexible a lead is, the less trauma is induced to the patient as a result of lead pressure. Furthermore, flexibility is an important consideration in light of the repeated movements of the heart, and also the tortuous path through which the lead is inserted. In addition, the outer body must be resistant to abrasive wear, for example, in the event that the lead rubs against another lead, implanted device, or anatomical structure while the lead is in use after it is implanted within a patient.

Some leads incorporate silicone as an insulator for the conductor. However, while silicone is a flexible and biostable material, silicone has poor tensile and wear characteristics. Furthermore, silicone has a high coefficient of friction, which is a drawback, for example when two leads are placed within the patient, or when silicone is used in proximity with moving parts.

Another consideration is the lead body diameter. Physicians prefer smaller leads because a smaller introducer can be used, and a smaller incision for the introducer is used. Furthermore, smaller leads are necessary when the relevant therapies require two or more leads to be implanted.

Accordingly, there is a need for a lead, which has improved flexibility. What is also needed is a lead having a smaller outer diameter that does not sacrifice insulation.

SUMMARY

A lead assembly is provided herein which includes a flexible lead body extending from a proximal end to a distal end, and the lead body includes two or more conductors disposed therein. A first conductor and a second conductor form two of the conductors, where the first conductor is co-axial and non co-radial with the second conductor. An electrode assembly is further included with the lead assembly. The electrode assembly includes at least one extendable and/or retractable electrode electrically coupled with one of the conductors. The second conductor is disposed within the first conductor, and the second conductor has a coating of insulation on the second conductor.

Several options for the lead assembly are as follows. For instance, in one option, the second conductor comprises one or more filars in a coiled configuration, and the one or more filars are coated with insulative material. In another option, the lead assembly further includes an insulative sleeve disposed between the first conductor and the second conductor, where the sleeve optionally comprises tubing. The lead assembly, in another option, further includes a means for facilitating rotation of the first conductor relative to the second conductor. In yet another option, the first conductor comprises one or more filars in a coiled configuration, and the one or more filars are coated with insulative material.

A lead assembly is provided herein which includes a flexible lead body extending from a proximal end to a distal end, and the lead body includes two or more conductors disposed therein. A first conductor and a second conductor form two of the conductors, and an electrode assembly is further included with at least one of the conductors of the lead assembly. The electrode assembly includes at least one extendable and/or retractable electrode electrically coupled with one of the conductors. The second conductor is disposed within the first conductor. The second conductor or the first conductor has a coating of insulation on its outer surface. A tubular insulative sleeve is disposed between the first conductor and the second conductor.

Several options for the lead assembly are as follows. For instance, in one option, the first conductor is co-axial and non co-radial with the second conductor. In another option, the first conductor and the second conductor include a coating of insulative material thereon. In yet another option, the second conductor is rotatable relative to the first conductor. In another option, the first conductor has a coiled configuration having an outer coil diameter, and the first conductor has an outer filar diameter, and a coating of EFTE or PFTE is disposed on the outer filar diameter. Optionally, in the lead assembly, the second conductor has a coiled configuration having an outer coil diameter, and the second conductor has an outer filar diameter, and a coating of EFTE or PFTE is disposed on the outer filar diameter.

In another embodiment, a method is provided herein. The method includes providing a second conductor having a coiled configuration having a second outer coil diameter, and the second conductor has a second outer filar diameter. The method further includes providing insulation on the second outer filar diameter, and disposing the second coiled conductor within a first coiled conductor to form a conductor assembly, where the first coiled conductor is non co-radial with the second coiled conductor. In addition, the method includes disposing the conductor assembly within a flexible lead body, coupling an electrode assembly with the first and/or the second conductor, and extending and/or retracting an at least one electrode from and/or within the flexible lead body.

Several options for the method are as follows. For instance, in one option, the method further includes disposing insulative tubing between the first conductor and the second conductor, and optionally further includes disposing insulation on a first outer filar diameter of the first conductor. In yet another option, the method further includes disposing polyimide or polyurethane tubing between the first conductor and the second conductor. In another option, the method further includes heat shrinking PTFE or ETFE on the second outer coil diameter.

In another embodiment, a method includes providing a second conductor having a coiled configuration having a second outer coil diameter, and the second conductor has a second outer filar diameter. The method further includes providing insulation on the second outer filar diameter, and disposing the second coiled conductor within a first coiled conductor to form a conductor assembly. In addition, the method includes disposing the conductor assembly within a flexible lead body, coupling an electrode assembly with the first and/or the second conductor, and disposing tubing between the first conductor and the second conductor.

Several options for the method are as follows. For instance, in one option, the method further includes extending and/or retracting the at least one electrode from and/or within the flexible lead body. In another option, the method further includes providing insulation on the second outer filar diameter. Optionally, the method includes heat shrinking PTFE or ETFE on the second outer coil diameter and over the insulation, and/or disposing insulation on a first outer filar diameter of the first conductor. In yet another option, the method includes disposing insulation on the first outer filar diameter of the first conductor.

The lead provides for a smaller lead body diameter due to the new manner in which insulation or layers of insulation are distributed within the lead body. For instance, smaller lead bodies, such as 6 French, are achievable. In addition, the above-described device allows for a secondary or redundant layer of insulation, for added reliability. The tubular sleeve, and also the ETFE/PTFE material or non-silicone material, facilitates rotation of the first conductor relative to the second conductor, for instance, for extending and/or retracting an electrode from and to the lead body.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
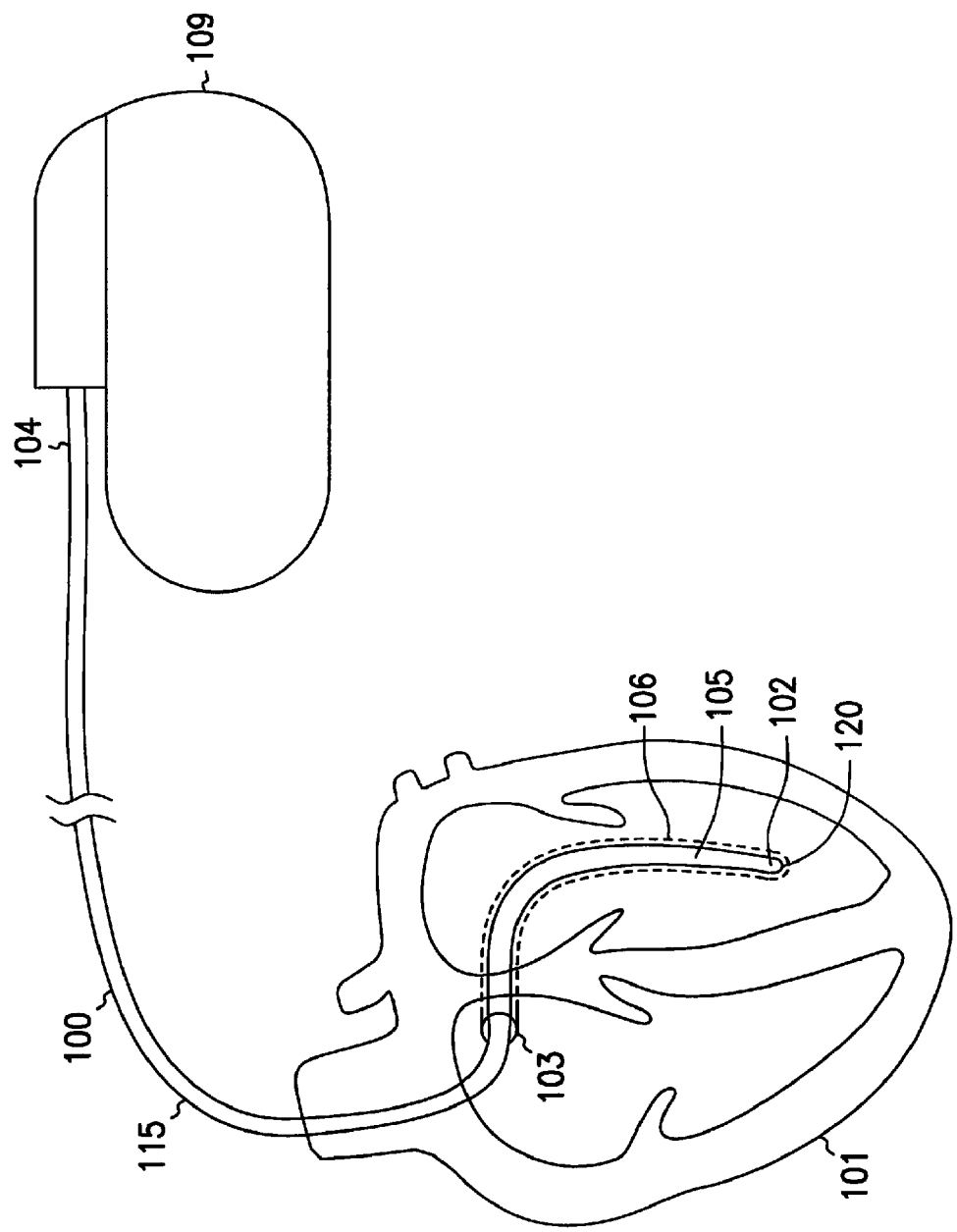
FIG. 1 illustrates a system for monitoring and stimulating the heart constructed in accordance with one embodiment.

FIG. 1 illustrates a system 200 for delivering electrical pulses to stimulate a heart 101 and/or for receiving electrical pulses to monitor the heart 101. The system 200 includes a pulse generator and signal sensor 109 and a lead 100. The lead 100 extends from a distal end 102 to a proximal end 104, and has an intermediate portion 105 therebetween. The distal end 102 is adapted for implantation within the heart of a patient and the proximal end 104 has a terminal connector, which electrically connects the various electrodes and conductors within the lead body 115 to a pulse generator and signal sensor 109. The pulse generator and signal sensor 109 contains electronics to sense various electrical signals of the heart and also produce current pulses for delivery to the heart 101. The pulse generator and signal sensor 109 is implanted pectorally, abdominally, or elsewhere within the patient.

The lead 100 includes a lead body 115, for instance a flexible lead body 115, at least one elongate conductor 160 (FIGS. 2-5) contained within the lead body 115, and at least one electrode 120 coupled with the lead 100. The lead body 115, as further described below, includes an elongate body formed of, for example, at least one polymer such as a medical grade silicone rubber for translumenal insertion and access within a living organism such as a patient. In one option, the lead body 115 is tubular and has an outer diameter that is small enough for translumenal insertion into the coronary sinus 103 and/or great cardiac vein 106.

The at least one electrode 120 is electrically coupled with the at least one elongate conductor 160 (FIGS. 2-5). The at least one electrode 120, in one option, is extendable and/or retractable from and/or to the lead body, such as a helix. Optionally, the at least one elongate conductor 160 comprises a coiled conductor and defines a lumen therein and thereby is adapted to receive a stiffening stylet that extends through the length of the lead 100.

The stylet is used to stiffen the lead 100, and is manipulated to facilitate the insertion of the lead 100 into and through a vein and through an intracardiac valve to advance the distal end 102 of the lead 100 into, for example, the ventricle of the heart 101. Optionally, a stylet knob is coupled with the stylet for rotating the stylet, advancing the conductor into tissue of the heart, and for manipulating the lead 100. Alternatively, the at least one elongate conductor 160 comprises other forms of conductors, such as a cable conductor, or a braided conductor as further discussed below.

Figure 2:
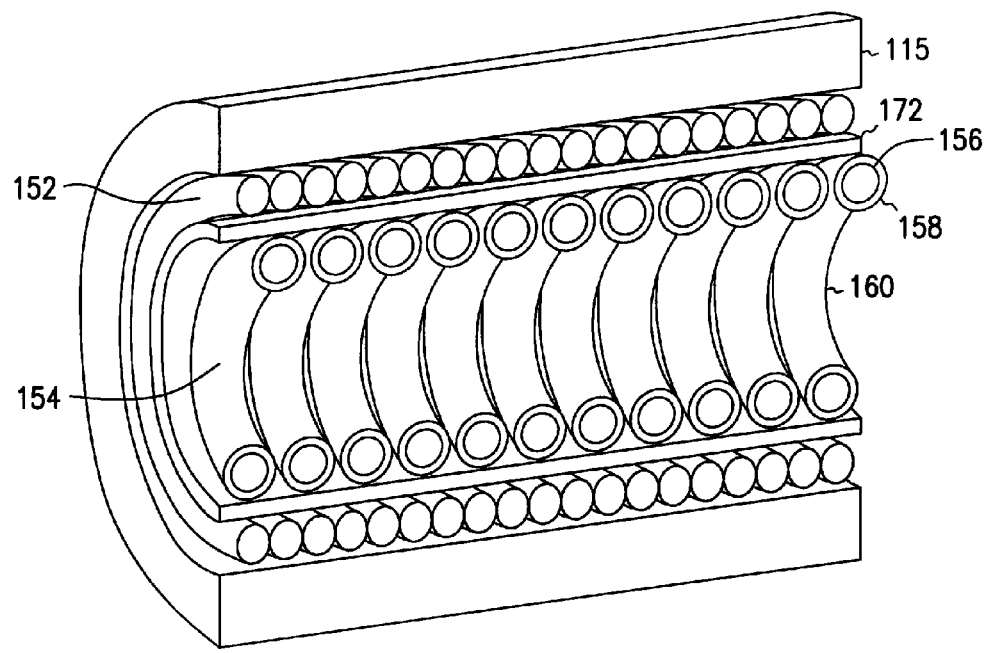
FIG. 2 is a cross-section of a portion of a lead assembly constructed in accordance with one embodiment.

FIG. 2 illustrates a portion of the lead shown in FIG. 1, including the lead 100, and/or the lead 100 and the pulse generator and signal sensor 109 (FIG. 1). The lead 100, in one option, is used to chronically stimulate the heart 101 (FIG. 1), such that the lead 100 is implanted on or about the heart 101 (FIG. 1) for long periods of time. As mentioned above, the lead body 115 includes an outer covering of insulation, and includes at least one elongate conductor 160. In one option, the elongate conductor 160 extends substantially along the entire length between the distal end 102 (FIG. 1) and the proximal end 104 (FIG. 1) of the lead 100. The at least one elongate conductor 160, in one option, includes a first outer conductor 152 and a second conductor 154. It should be noted that the at least one elongate conductor 160 optionally includes two or more conductors which are co-radial or are non-co-radial with each other.

The first outer conductor 152, in one option, is co-axial but not co-radial with the second conductor 154, for example, the first outer conductor 152 and/or the second conductor 154 have a coiled configuration. For example, the second conductor 154 is disposed within the first outer conductor 152. In another option, the second conductor 154 includes one or more filars, which collectively have a second outer filar diameter 156. The second outer filar diameter 156 optionally includes a layer of insulation 158. Suitable materials for the layer of insulation 158 include, but are not limited to, PTFE, ETFE, or polyimide.

In one option, an inner sleeve of insulation 172 is disposed between the first outer conductor 152 and the second conductor 154. The inner sleeve of insulation 172 is in addition to the lead body 115. The inner sleeve of insulation 172, in one option, is disposed adjacent to the first outer conductor 152 and to the second conductor 154. In another option, the inner sleeve of insulation 172 comprises a tube of material. Suitable materials for the inner layer of insulation 172 include, but are not limited to, polyurethane or polysiloxane urethane, or a non-silicone material. In yet another option, the one or more conductors are co-radial, and the outer conductor includes a coating of insulation, such as ETFE, PTFE, or polyimide. The inner insulation 172 may or may not rotate with the second conductor 154 when it is used to rotate or extend or retract the electrode.

Figure 3:
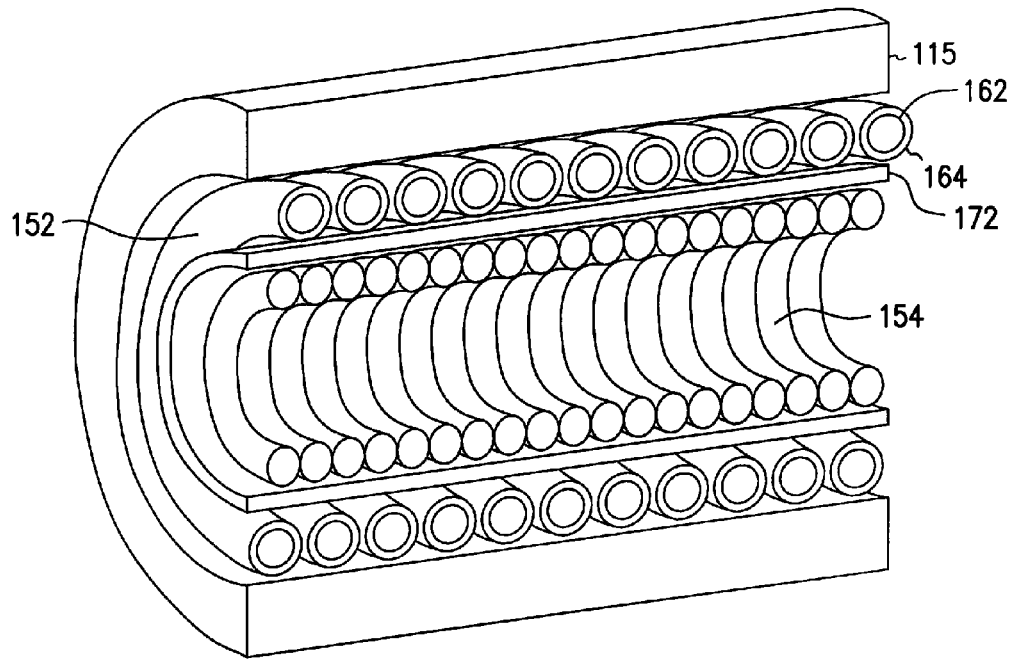
FIG. 3 is a cross-section of a portion of a lead assembly constructed in accordance with one embodiment.

Referring to FIG. 3, the first outer conductor 152, in one option, is co-axial but not co-radial with the second conductor 154, for instance the first outer conductor 152 and/or the second conductor 154 are in a coiled configuration. For example, the second conductor 154 is disposed within the first outer conductor 152. In another option, the first outer conductor 152 includes one or more filars, which collectively have a first outer filar diameter 162. The first outer filar diameter 162 optionally includes a layer of insulation 164. Suitable materials for the layer of insulation 164 include, but are not limited to, PTFE, ETFE, or polyimide. In yet another option, the one or more conductors are co-radial, and the outer conductor includes a coating of insulation, such as ETFE, PTFE, or polyimide.

In one option, an inner sleeve of insulation 172 is disposed between the first outer conductor 152 and the second conductor 154. The inner sleeve of insulation 172 is in addition to the lead body 115. The inner sleeve of insulation 172, in one option, is disposed adjacent to the first outer conductor 152 and to the second conductor 154. In another option, the inner sleeve of insulation 172 comprises a tube of material. Suitable materials for the inner layer of insulation 172 include, but are not limited to, polyurethane, polyimide, polysiloxane urethane, or a non-silicone material.

Figure 4:
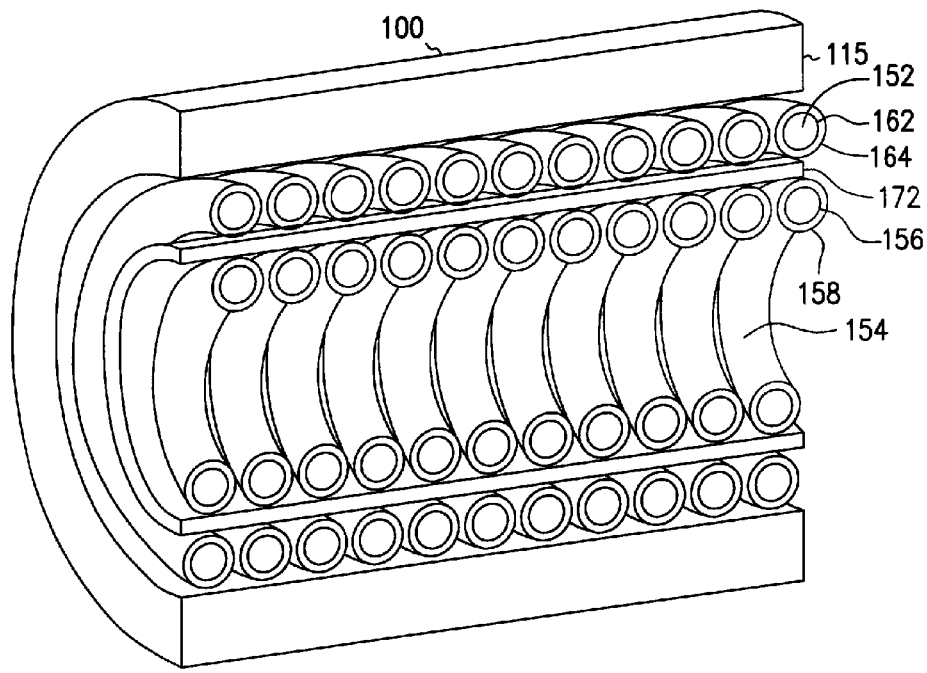
FIG. 4 is a cross-section of a portion of a lead assembly constructed in accordance with one embodiment.

FIG. 4 illustrates another embodiment of the lead 100 (FIG. 1). The lead 100 includes the first outer conductor 152 and the second conductor 154. The first outer conductor 152, in one option, is co-axial but not co-radial with the second conductor 154, for instance the first outer conductor 152 and/or the second conductor 154 are in a coiled configuration. For example, the second conductor 154 is disposed within the first outer conductor 152. In another option, the first outer conductor 152 includes one or more filars, which collectively have a first outer filar diameter 162. The first outer filar diameter 162 optionally includes a layer of insulation 164. Suitable materials for the layer of insulation 164 include, but are not limited to, PTFE, ETFE, or polyimide. In another option, the second conductor 154 includes one or more filars, which collectively have a second outer filar diameter 156. The second outer filar diameter 156 optionally includes a layer of insulation 158. Suitable materials for the layer of insulation 158 include, but are not limited to, PTFE, ETFE, or polyimide.

An inner sleeve of insulation 172 is disposed between the first outer conductor 152 and the second conductor 154. The inner sleeve of insulation 172 is in addition to the lead body 115. The inner sleeve of insulation 172, in one option, is disposed adjacent to the first outer conductor 152 and to the second conductor 154. In another option, the inner sleeve of insulation 172 comprises a tube of material. Suitable materials for the inner layer of insulation 172 include, but are not limited to, polyurethane or polysiloxane urethane. The inner layer of insulation 172 may or may not rotate with the second inner conductor 154 when it is used to rotate, extend, or retract the electrode.

Figure 5:
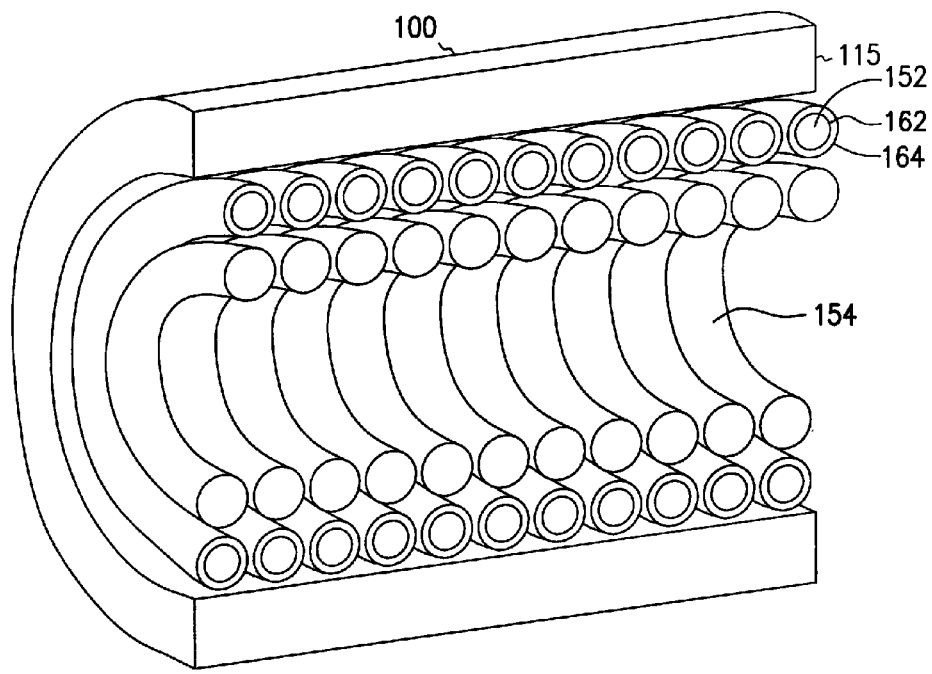
FIG. 5 is a cross-section of a portion of a lead assembly constructed in accordance with one embodiment.

FIG. 5 illustrates yet another embodiment of the lead 100. The lead 100 includes the first outer conductor 152 and the second conductor 154. The first outer conductor 152, in one option, is co-axial but not co-radial with the second conductor 154, for instance the first outer conductor 152 and/or the second conductor 154 are in a coiled configuration. For example, the second conductor 154 is disposed within the first outer conductor 152. In another option, the first outer conductor 152 includes one or more filars, which collectively have a first outer filar diameter 162. The first outer filar diameter 162 includes a layer of insulation 164. Suitable materials for the layer of insulation 164 include, but are not limited to, PTFE, ETFE, or polyimide.

Figure 6:
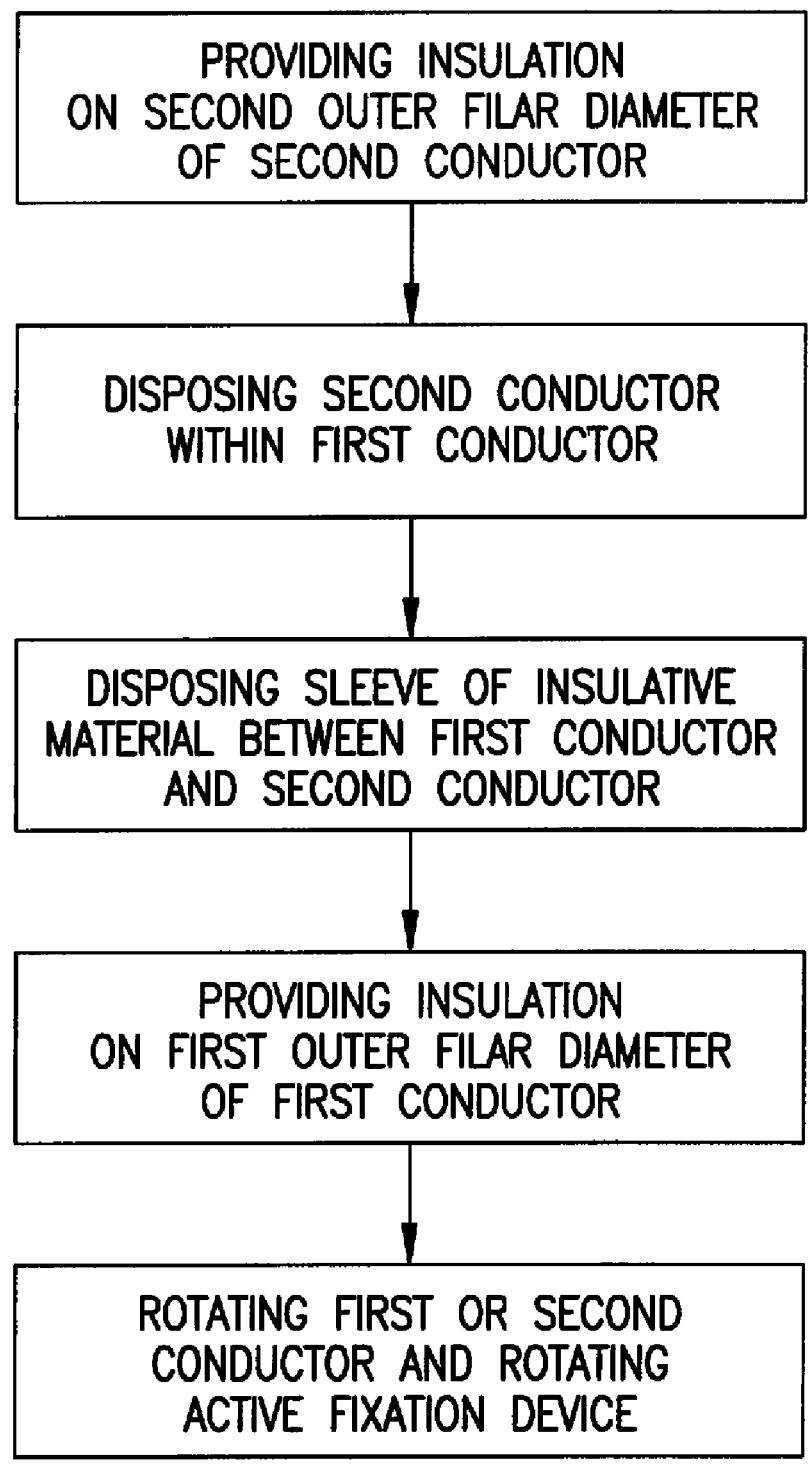
FIG. 6 is a block diagram illustrating a method in accordance with another embodiment.

Referring to FIG. 6, a block diagram is shown illustrating a method, which includes, in one option, providing insulation on a second outer filar diameter of a second conductor. The method further includes disposing the second conductor within the first conductor, and disposing a sleeve of insulative material between the first conductor and the second conductor. The method optionally includes providing insulation on the first outer filar diameter of the first conductor, and further optionally includes rotating the first or second conductor and rotating active fixation device. The insulative materials, specifics of which are further discussed above, facilitate the movement of the first conductor relative to the second conductor, and further facilitate extension and retraction of the electrode.

In another embodiment, a method includes providing a second conductor having a coiled configuration having a second outer coil diameter, and the second conductor has a second outer filar diameter. The method further includes providing insulation on the second outer filar diameter, and disposing the second coiled conductor within a first coiled conductor to form a conductor assembly, where the first coiled conductor is non co-radial with the second coiled conductor. In addition, the method includes disposing the conductor assembly within a flexible lead body, coupling an electrode assembly with the first and/or the second conductor, and extending and/or retracting an at least one electrode from and/or within the flexible lead body.

Several options for the method are as follows. For instance, in one option, the method further includes disposing insulative tubing between the first conductor and the second conductor, and optionally further includes disposing insulation on an first outer filar diameter of the first conductor. In yet another option, the method further includes disposing polyimide or polyurethane tubing between the first conductor and the second conductor. In another option, the method further includes heat shrinking PTFE or ETFE on the second outer coil diameter.

In another embodiment, a method includes providing a second conductor having a coiled configuration having a second outer coil diameter, and the second conductor has a second outer filar diameter. The method further includes providing insulation on the second outer filar diameter, and disposing the second coiled conductor within a first coiled conductor to form a conductor assembly. In addition, the method includes disposing the conductor assembly within a flexible lead body, coupling an electrode assembly with the first and/or the second conductor, and disposing tubing between the first conductor and the second conductor.

Several options for the method are as follows. For instance, in one option, the method further includes extending and/or retracting the at least one electrode from and/or within the flexible lead body. In another option, the method further includes providing insulation on the second outer filar diameter. Optionally, the method includes heat shrinking PTFE or ETFE on the second outer coil diameter and over the insulation, and/or disposing insulation on an first outer filar diameter of the first conductor. In yet another option, the method includes disposing insulation on the first outer filar diameter of the first conductor.

Advantageously, the above-described lead provides for a smaller lead body diameter due to the new manner in which insulation or layers of insulation are distributed within the lead body. For instance, smaller lead bodies, such as 6 French, are achievable. In addition, the above-described device allows for a secondary or redundant layer of insulation, for added overall reliability. Furthermore, the tubular sleeve provides a cost efficient lead design, which further improves ease of manufacturability. The tubular sleeve, and also the ETFE/PTFE material or non-silicone material, facilitates rotation of the first conductor relative to the second conductor, for instance, for extending and/or retracting an electrode from and to the lead body.

It is to be understood that the above description is intended to be illustrative, and not restrictive. For instance, the leads described above include, but are not limited to, tachy, brady, or coronary sinus leads. It should be noted that features of the various above-described embodiments may be interchanged to form additional combinations. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead assembly comprising:
    a lead body extending from a proximal end to a distal end, the lead body including two or more co-axial and non co-radial conductors disposed therein;
    the two or more co-axial and non co-radial conductors including a first conductor and a second conductor, the second conductor disposed within, and rotatable relative to, the first conductor;
    the first conductor including one or more filars having a coating of insulation disposed directly on an outer surface portion thereof; and
    an electrode assembly including at least one extendable and/or retractable electrode electrically coupled with at least one of the conductors.

2. The lead assembly of claim 1, further comprising an insulative sleeve disposed between the first conductor and the second conductor.

3. The lead assembly of claim 2, wherein the insulative sleeve includes a tube of material disposed between the first conductor and the second conductor.

4. The lead assembly of claim 2, wherein the insulative sleeve includes at least one of polyurethane, polyimide, polysiloxane urethane, or a non-silicone material.

5. The lead assembly of claim 1, further comprising a means for facilitating rotation of the second conductor relative to the first conductor.

6. The lead assembly of claim 1, wherein the one or more filars of the first conductor are disposed in a coiled configured.

7. The lead assembly of claim 1, wherein the coating of insulation disposed directly on the outer surface portion of the first conductor includes at least one of PTFE, ETFE, or polyimide.

8. The lead assembly of claim 1, wherein the second conductor includes one or more filars having a coating of insulation disposed directly on an outer surface portion thereof.

9. The lead assembly of claim 1, wherein a cross-sectional size of the lead body is about 6 French or less.

10. A lead assembly comprising:
    a lead body extending from a proximal end to a distal end, the lead body including two or more conductors disposed therein;
    the two or more conductors including a first conductor and a second conductor, the second conductor disposed within, and rotatable relative to, the first conductor;
    a coating of insulation disposed directly on an outer surface portion of the first conductor; and
    an electrode assembly including at least one extendable and/or retractable electrode electrically coupled with at least one of the conductors.

11. The lead assembly of claim 10, further comprising a tubular insulative sleeve disposed between the first conductor and the second conductor.

12. The lead assembly of claim 11, wherein the tubular insulative sleeve includes at least one of polyurethane, polyimide, polysiloxane urethane, or a non-silicone material.

13. The lead assembly of claim 10, further comprising a terminal connector at the proximal end of the lead body, the terminal connector including a driving portion for facilitating rotation of the second conductor relative to the first conductor.

14. The lead assembly of claim 10, wherein the first conductor is co-axial and non co-radial with the second conductor.

15. The lead assembly of claim 10, wherein the coating of insulation disposed directly on the outer surface portion of the first conductor includes at least one of PTFE, ETFE, or polyimide.

16. The lead assembly of claim 10, wherein the second conductor includes a coating of insulation disposed directly on an outer surface portion thereof.

17. The lead assembly of claim 10, wherein the first conductor includes one or more filars having a coiled configuration, the one or more filars including the coating of insulation disposed directly on an outer surface portion thereof.

* * * * *